United States Patent
Shirai (10) Patent No.: US 10,161,855 B2
(45) Date of Patent: Dec. 25, 2018

(54) OPTICAL TOMOGRAPHIC IMAGING METHOD, OPTICAL TOMOGRAPHIC IMAGING APPARATUS, AND PROGRAM

(71) Applicant: NATIONAL INSTITUTE OF ADVANCED INDUSTRIAL SCIENCE AND TECHNOLOGY, Tokyo (JP)

(72) Inventor: Tomohiro Shirai, Tsukuba (JP)

(73) Assignee: NATIONAL INSTITUTE OF ADVANCED INDUSTRIAL SCIENCE AND TECHNOLOGY (JP)

(*) Notice: Subject to any disclaimer, the term of this patent is extended or adjusted under 35 U.S.C. 154(b) by 94 days.

(21) Appl. No.: 15/518,606

(22) PCT Filed: Sep. 17, 2015

(86) PCT No.: PCT/JP2015/076475
§ 371 (c)(1),
(2) Date: Apr. 12, 2017

(87) PCT Pub. No.: WO2016/059939
PCT Pub. Date: Apr. 21, 2016

(65) Prior Publication Data
US 2017/0219482 A1 Aug. 3, 2017

(30) Foreign Application Priority Data

Oct. 16, 2014 (JP) .................. 2014-211547

(51) Int. Cl.
*G01B 9/02* (2006.01)
*G01N 21/17* (2006.01)
(Continued)

(52) U.S. Cl.
CPC ........... *G01N 21/17* (2013.01); *A61B 5/0073* (2013.01); *G01B 9/021* (2013.01);
(Continued)

(58) Field of Classification Search
CPC .............. A61B 5/0073; G01B 9/02044; G01B 9/02058; G01B 9/02063; G01B 9/02079;
(Continued)

(56) References Cited

U.S. PATENT DOCUMENTS

2004/0239946 A1 12/2004 Kane et al.
2006/0087616 A1 4/2006 Hanebuchi .................... 351/210
(Continued)

FOREIGN PATENT DOCUMENTS

JP 2004-512538 4/2004
JP 2006-122649 A 5/2006
(Continued)

OTHER PUBLICATIONS

International Search Report dated Dec. 28, 2015 in corresponding PCT International Application No. PCT/JP2015/076475.
(Continued)

*Primary Examiner* — Mark R Gaworecki
(74) *Attorney, Agent, or Firm* — Ostrolenk Faber LLP (57) ABSTRACT

In a measurement by means of OCT, when dispersion is present in a measured target or an optical system in the vicinity of the measured target, resolution of the measurement is degraded. One spectral interference fringe intensity is acquired when a phase difference between measurement light and reference light is not introduced, two spectral interference fringe intensities are acquired in a time-series manner when a phase difference of $\pi$ is introduced, a required calculation is performed based on the intensity, and a tomographic image not having reduced resolution due to dispersion is acquired.

20 Claims, 6 Drawing Sheets

(51) Int. Cl.
 *A61B 5/00* (2006.01)
 *G01B 9/021* (2006.01)
(52) U.S. Cl.
 CPC ..... *G01B 9/02044* (2013.01); *G01B 9/02058* (2013.01); *G01B 9/02063* (2013.01); *G01B 9/02079* (2013.01); *G01B 9/02087* (2013.01); *G01B 9/02091* (2013.01); *G01N 2021/1787* (2013.01); *G06T 2207/10101* (2013.01)
(58) Field of Classification Search
 CPC ............ G01B 9/02087; G01B 9/02091; G01B 9/021; G01N 21/17; G01N 2021/1787; G06T 2207/10101
 See application file for complete search history.

(56) References Cited

U.S. PATENT DOCUMENTS

| | | | |
|---|---|---|---|
| 2007/0086011 A1 | 4/2007 | Toida | 356/450 |
| 2010/0231917 A1 | 9/2010 | Izatt et al. | 356/456 |
| 2012/0113431 A1 | 5/2012 | Fukuma et al. | 356/456 |
| 2012/0188555 A1 | 7/2012 | Izatt et al. | 356/479 |
| 2013/0242309 A1 | 9/2013 | Yuan et al. | 356/479 |
| 2014/0125992 A1 | 5/2014 | Ota | 356/497 |

FOREIGN PATENT DOCUMENTS

| | | |
|---|---|---|
| JP | 2007-101250 A | 4/2007 |
| JP | 2007-508558 A | 4/2007 |
| JP | 2007-267927 A | 10/2007 |
| JP | 2010-268916 | 12/2010 |
| JP | 2010-279508 A | 12/2010 |
| JP | 2011-528111 | 11/2011 |
| JP | 2012-010775 A | 1/2012 |
| JP | 2012-210358 A | 11/2012 |
| JP | 2013-190412 A | 9/2013 |
| JP | 2014-092425 A | 5/2014 |
| JP | 5558735 B | 7/2014 |
| WO | WO 02/36015 A1 | 5/2002 |
| WO | WO 2005/040718 A1 | 5/2005 |
| WO | WO 2010/006785 A1 | 1/2010 |

OTHER PUBLICATIONS

Written Opinion dated Dec. 28, 2015 in corresponding PCT International Application No. PCT/JP2015/076475.
A.F. Fercher et al., "Optical coherence tomography—principles and applications," Reports on Progress in Physics, vol. 66, pp. 239-303 (2003).
T. Shirai et al., "Intensity-interferometric spectral-domain optical coherence tomography with dispersion cancellation," Journal of the Optical Society of America, Part A, vol. 31, pp. 258-263 (2014).
S. Suja Helen et al., "Achromatic phase shifting by a rotating polarizer," Optics Communications, vol. 154, pp. 249-254 (1998).
Tomohiro, Shirai et al., "Resolution improvement in spectral-domain optical coherence tomography based on classical intensity correlations", Optics Letters, Optical Society of America, vol. 38, No. 2, pp. 115-117 (2013).
Ryczkowski Piotr et al. "Experimental confirmation of dispersion-free intensity optical coherence tomography" 2014 16$^{th}$ International Conference on Transparent Optical Networks (ICTON), IEEE, pp. 1-2 (2014).
Tomohiro Shirai "Modifications of intensity-interferometric spectral-domain optical coherence tomography with dispersion cancellation" Journal of Optics, Institute of Physics Publishing Bristol GB, vol. 17, No. 4, p. 45605 (2015).

OPTICAL TOMOGRAPHIC IMAGING METHOD, OPTICAL TOMOGRAPHIC IMAGING APPARATUS, AND PROGRAM

CROSS-REFERENCE TO RELATED APPLICATIONS

The present application is a 35 U.S.C. §§ 371 national phase conversion of PCT/JP2015/076475, filed Sep. 17, 2015, which claims priority to Japanese Patent Application No. 2014-211547, filed Oct. 16, 2014, the contents of which are incorporated herein by reference. The PCT International Application was published in the Japanese language.

TECHNICAL FIELD

The present invention relates to a method and an apparatus of acquiring a tomographic image of a measured target such as biological tissues by using coherency of light waves.

BACKGROUND

A measurement principle that acquires a tomographic image by using coherency of light waves is called optical coherence tomography (OCT) and is currently in practical use as medical apparatuses that acquire tomographic images of retinas (for example, refer to Patent Document 1 and Non-patent Document 1).

In the apparatus, light having low coherency is separated into measurement light and reference light, a measured object is arranged on the measurement light side, a reference mirror is arranged on the reference light side, reflection light from the measured object and reflection light from the reference mirror are superposed to obtain an interference signal, and thereby, a tomographic image is acquired. Therefore, it is possible to obtain higher depth resolution (hereinafter, resolution) as the coherency is lower, that is, the spectral width of a light source is wider.

The apparatuses can be generally classified into time-domain OCT (TD-OCT) and spectral-domain OCT (SD-OCT), and currently, SD-OCT in which mechanical scanning of the reference mirror is unnecessary by spectroscopically analyzing the interference signal when acquiring a tomographic image is the mainstream.

In general, OCT has a feature that the resolution is degraded when group velocity dispersion (hereinafter, dispersion) that is present on a measurement optical path is different from dispersion that is present on a reference optical path. Therefore, when a measured target or an optical system in the vicinity of the measured target has dispersion, there is a disadvantage that the resolution may be degraded due to the effect of the dispersion.

Recently, SD-OCT has been upgraded to develop an intensity-interferometric spectral-domain tomographic imaging apparatus that automatically cancels, even when the dispersion that is present on the measurement optical path is different from dispersion that is present on the reference optical path, the effect of the dispersion (refer to Non-patent Document 2).

The principle of the apparatus is similar to that of SD-OCT; however, the apparatus has a relatively complicated and large configuration in which, for example, two spectroscope devices are required compared to usual SD-OCT.

RELATED ART DOCUMENTS

Patent Documents

[Patent Document 1] Japanese Patent No. 5558735
[Patent Document 2] Japanese Patent Application, Publication No. 2007-267927

Non-Patent Documents

[Non-patent Document 1] A. F. Fercher, W. Drexler, C. K. Hitzenberger, and T. Lasser, "Optical coherence tomography—principles and applications," Reports on Progress in Physics, vol. 66, pp. 239-303, (2003).
[Non-patent Document 2] T. Shirai and A. T. Friberg, "Intensity-interferometric spectral-domain optical coherence tomography with dispersion cancellation," Journal of the Optical Society of America, Part A, vol. 31, pp. 258-263 (2014).
[Non-patent Document 3] S. S. Helen, M. P. Kothiyal, and R. S. Sirohi, "Achromatic phase shifting by a rotating polarizer," Optics Communications, vol. 154, pp. 249-254 (1998).

SUMMARY OF INVENTION

Technical Problem

Generally, it is known that the measurement using OCT has a feature that resolution is degraded when dispersion that is present on a measurement optical path is different from dispersion that is present on a reference optical path. Therefore, when dispersion is present in a measured target or in an optical system (that is, in a measurement optical path) in the vicinity of the measured target, the resolution is degraded.

In order to prevent the degradation of the resolution, in the related art, a method has been used in which dispersion that is completely the same as the dispersion that is present on the measurement optical path is introduced to the reference optical path by design to cancel the effect (for example, refer to Patent Document 2).

However, in this method, it is difficult to completely cancel the effect with respect to a measured target having unknown or complicated dispersion properties, and therefore, degradation of the resolution is inevitable when measuring such a measured target.

Figure 5:
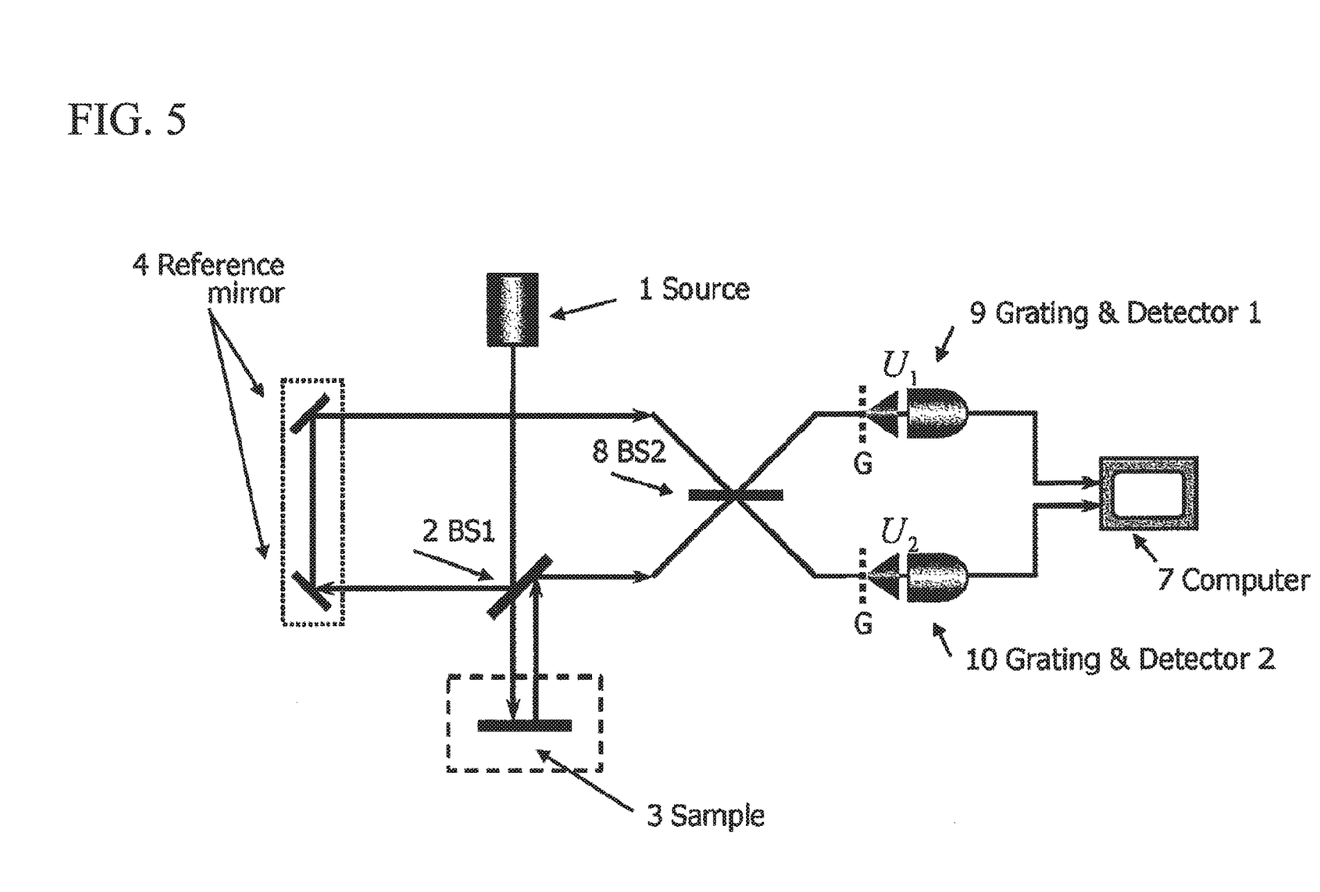
FIG. 5 is a view showing an optical system of an intensity-interferometric spectral-domain tomographic imaging apparatus in the related art. In the drawing, each arrow indicates a light travel path.

As a novel principle for solving the problem, recently, an intensity-interferometric spectral-domain tomographic imaging apparatus shown in FIG. 5 has been proposed in which, even when unknown or complicated dispersion is present, the dispersion is automatically cancelled to prevent the resolution from being degraded; however, the apparatus has a complicated configuration in which, for example, two spectroscope devices are required in principle.

Solution to Problem

As a method of realizing this, similarly to an SD-OCT apparatus, using one spectroscope device, the present invention provides a method and an apparatus of: acquiring an intensity of a spectral interference fringe (interference fringe obtained by wavelength decomposition, with a spectroscope device, of an interference signal due to broadband light) when a phase difference between measurement light and reference light is not introduced and an intensity of a spectral interference fringe when a phase difference of $\pi$ is introduced in a time-series manner; performing necessary calculation based on the two intensities; and acquiring tomographic information.

Further, the present invention provides a method and an apparatus of: extending an analysis method of the above-described spectral interference fringe intensity data acquired by two measurements having the phase difference; and acquiring tomographic information having resolution of the same level by analyzing spectral interference fringe intensity data on the basis of a simpler single measurement.

A method of generating a phase difference of π between the measurement light and the reference light includes: locating a measured target or a reference mirror on a fine motion stage; and moving the stage in a frontward direction or a rearward direction along the propagation direction of light by a distance half of the center wavelength of a light source.

In this method, the phase difference with respect to light having a wavelength other than the center wavelength does not strictly become π, and therefore, errors occur as the spectrum of the light source is broadened.

On the other hand, as a method of generating a similar phase difference, it is possible to use a method of controlling polarization states of the measurement light and the reference light and using the change of a geometric phase accompanied by the control (for example, refer to Nonpatent Document 3).

In this method, phase shift which is independent of the spectrum is available, and therefore, errors which depend on the spectral width of the light source do not occur.

It is known that, when acquiring a tomographic image of a general measured target based on the principle, an unnecessary image (hereinafter, referred to as an artifact) occurs even at a position where an object (measured target) is not actually present. In order to remove the artifact, a plurality of data may be acquired, and an averaging process may be added.

Advantage of the Invention

One spectroscope device is sufficient, and therefore, the entire apparatus can be realized at low cost compared to the apparatus configuration in the related art that uses two spectroscope devices.

Further, optical adjustment can be performed easier compared to the apparatus configuration in the related art that uses two spectroscope devices, and it is possible to reduce a factor that causes measurement errors.

By adding slight improvement change to SD-OCT apparatuses that have been already widely used, it is possible to realize an intensity-interferometric spectral-domain tomographic imaging apparatus that is unaffected by dispersion. That is, at the time of commercialization, not distribution as an independent apparatus but distribution as an option that upgrades the existing OCT apparatuses is available.

As a basic performance of an intensity-interferometric spectral-domain tomographic imaging apparatus, the resolution can be improved about 1.4 times compared to a general SD-OCT apparatus when a light source having completely the same spectral width is used.

BRIEF DESCRIPTION OF THE DRAWINGS

Part (a) of FIG. 6 is a view showing an experimental result of the present invention acquired without adding a mechanism or means for generating a phase difference π between measurement light and reference light when a simple reflection mirror is a measured target. Part (b) of FIG. 6 is a view showing a similar experimental result when the dispersion medium (dense flint glass) is arranged on the measurement optical path immediately before the measured target. A converted value of a pixel to a length in (a) and (b) is half of that in the SD-OCT apparatus of FIG. 3(*a*).

Part (a) of FIG. 7 represents a signal acquired before moving a detector, and part (b) of FIG. 7 represents a signal acquired after moving the detector by a distance of about six pixels. A converted value of a pixel to a length is half of that in the SD-OCT apparatus of FIG. 3(*a*).

DESCRIPTION OF EMBODIMENTS

Calculations (using Expression (2) or Expression (4)) that realize the principle are performed with adding (Embodiment 1) or without adding (Embodiment 3) a mechanism or means that generates a phase difference π between measurement light and reference light to an existing SD-OCT apparatus, and a tomographic image of a measured target is generated.

Embodiment 1

Figure 1:
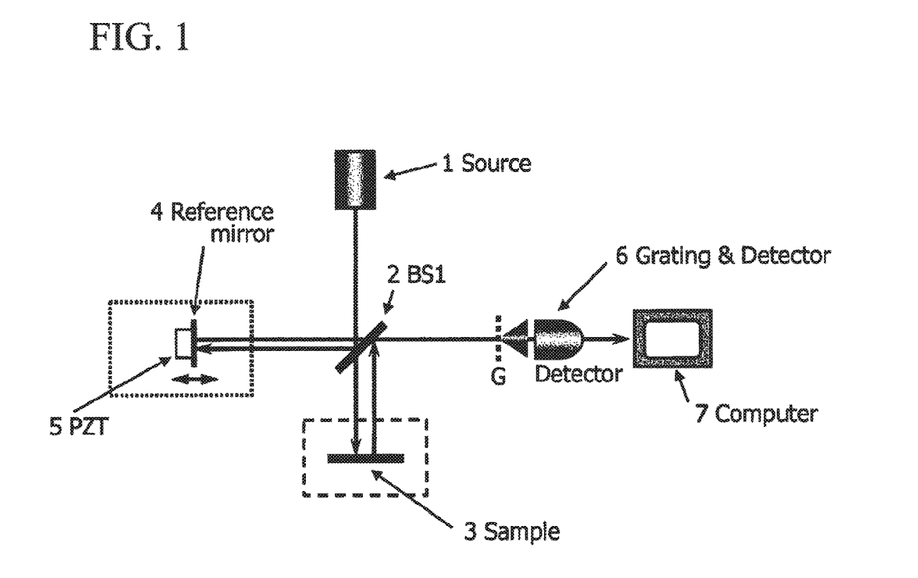
FIG. 1 is a view showing an optical system of an intensity-interferometric spectral-domain tomographic imaging apparatus proposed by the present invention. In the drawing, each arrow indicates a light travel path.
Figure 2:
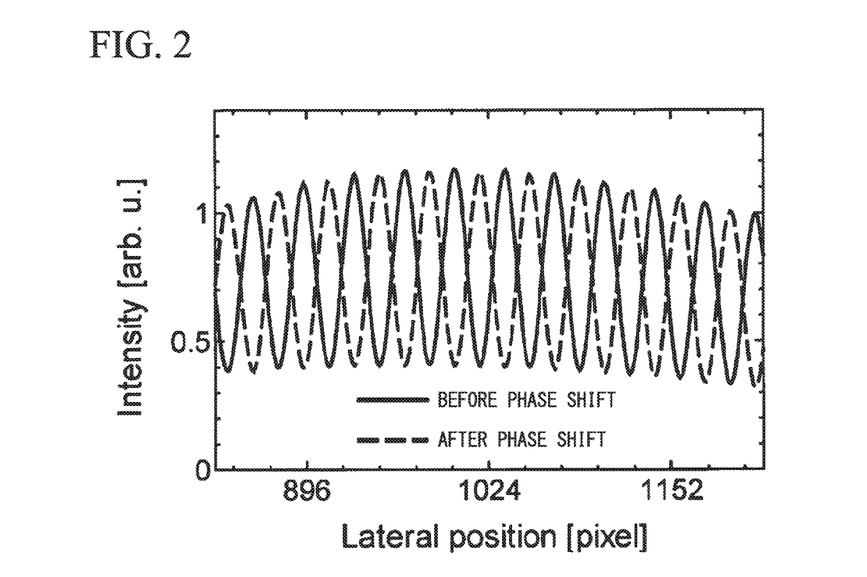
FIG. 2 is a view showing the intensity of spectral interference fringes of which phases are different by π from each other and which are acquired before and after movement of a fine motion stage.

FIG. 1 shows an optical system of an intensity-interferometric spectral-domain tomographic imaging apparatus proposed by the present invention. In the drawing, each arrow indicates a light travel path.

This optical system is basically the same as that of a conventional SD-OCT apparatus but has a difference that a reference mirror is located on a fine motion stage which is driven by a piezo element so as to be vertically illuminated by incident light, and the fine motion stage is movable frontward and rearward along the propagation direction of light.

In the drawing, a spectroscope device is formed by combining a diffraction grating G and a detector; however, a spectroscope device of another type may be similarly formed by combining a spectroscope element and a detector in general. The drive method of the fine motion stage is not limited to a piezo element.

FIG. 1 shows a configuration of a Michelson interferometer formed of a light source, a beam splitter, a reference mirror, a measured target, and a detector; however, an interferometer of another type is similarly available. The beam splitter may be a demultiplexer/multiplexer and can be formed using a 2×2 optical fiber coupler.

Light from a broadband light source having a broad spectral width is separated into reference light and measurement light by a beam splitter BS1. The light source is, for example, a super-luminescent diode or super-continuum light source; however, a light source of another type may be used as long as the spectrum is broad.

The reference light is reflected by the reference mirror, the measurement light is reflected by the measured target, and return light from the reference mirror and return light from the measured target are multiplexed by the beam splitter BS1 to interfere.

The interference light is decomposed into a spectrum by the diffraction grating, and spectral interference fringe intensity is detected by the detector.

The reference mirror is located on the fine motion stage.

First, spectral interference fringe intensity before moving the fine motion stage is detected and is stored in a computer (including a display device).

In general, when light is decomposed into a spectrum using a diffraction grating, the intensity is detected by a detector as a function of a wavelength λ, and therefore, this is converted into an intensity as a function of a frequency a by using Expression (1) (c is the velocity of light).

$$\omega=2\pi c/\lambda \quad (1)$$

The obtained intensity is represented by $I_1(\omega)$.

When the spectral interference fringe intensity is detected, adjustment is performed in advance such that a center frequency $\omega_0$ of incident light is matched to the center of the detector.

Next, the fine motion stage described above is moved in a frontward direction or a rearward direction along the propagation direction of light waves by a distance half of the center wavelength of the incident light (that is, the phase of the reference light is shifted by π), spectral interference fringe intensity is detected and is stored in a computer (including a display device) similarly as described above, and similar conversion is performed. The obtained intensity is represented by $I_2(\omega)$.

The spectral interference fringe intensity before phase shift at a frequency shifted in a positive direction by ω' from the center frequency $\omega_0$ is $I_1(\omega_0+\omega')$. The spectral interference fringe intensity after phase shift at a frequency shifted in a negative direction by ω' from the center frequency $\omega_0$ is $I_2(\omega_0-\omega')$. The product of $I_1(\omega_0+\omega')$ and $I_2(\omega_0-\omega')$ is represented by Expression (2).

$$C(\omega')=I_1(\omega_0+\omega')\times I_2(\omega_0-\omega') \quad (2)$$

Fourier transform of C(ω') as a function of ω' is performed with respect to ω' in the computer (including a display device).

As a result, the Fourier transform of C(ω') generally gives complex values, and an aimed signal having information about the position and the reflectivity of the measured target is obtained in the real part of the Fourier transform of C(ω').

On the other hand, when the absolute value of the Fourier transform of C(ω') is evaluated, an unnecessary signal adjacent to the above aimed signal is also observed. However, the unnecessary signal appears in the imaginary part of the Fourier transform of C(ω'), and therefore, it is possible to easily separate the aimed signal and the unnecessary signal.

Figure 3:
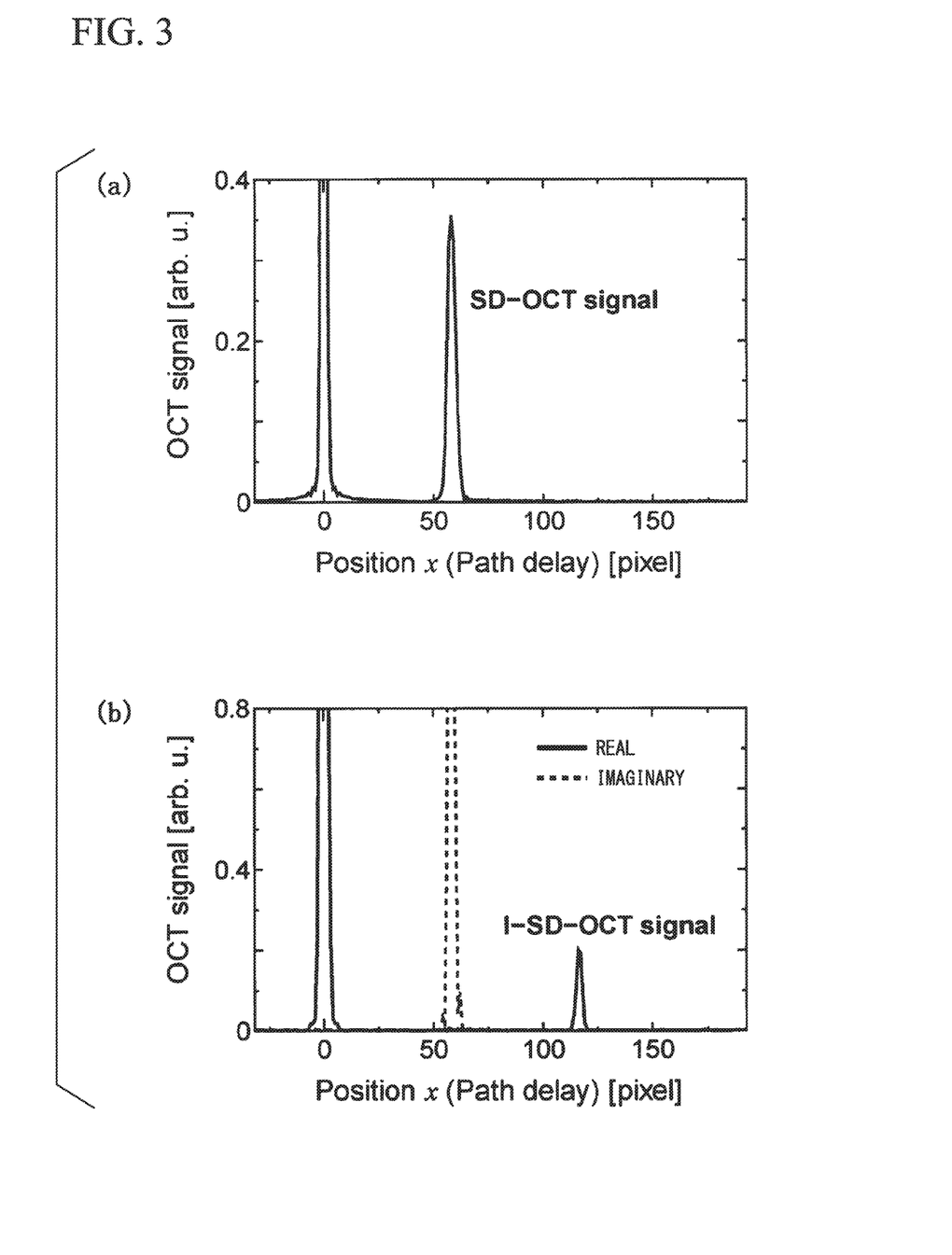
FIG. 3 is a view for comparing an experimental result of a SD-OCT apparatus (a) and an experimental result of the present invention (b) when a simple reflection mirror is a measured target. A converted value of a pixel to a length in the present invention (b) is half of that in the SD-OCT apparatus (a).

FIG. 3 shows absolute values of two signals which are the real part and the imaginary part of the Fourier transform of C(ω') obtained by the above calculation process.

Part (a) of FIG. 3 represents an experimental result acquired using a conventional SD-OCT apparatus when a simple reflection mirror is located as the measured target. Part (b) of FIG. 3 represents an experimental result acquired by the proposed apparatus.

In conventional SD-OCT, a signal that depends on the reflectivity and the position of the reflection mirror employed as the measured target is observed in the vicinity of the horizontal axis x=60. Specifically, the height of the signal is proportional to the reflectivity of the measured target (reflection mirror), and the position of the signal is proportional to the difference between a distance to the measured target (reflection mirror) from the beam splitter and a distance to the reference mirror from the beam splitter. Therefore, when the difference between the distances becomes large, the signal appears not in the vicinity of x=60 but in the vicinity of a larger x value. The signal in the vicinity of x=0 represents a bias component of the interference signal and includes no information about the measured target.

On the other hand, in the proposed apparatus, a signal that depends on the reflectivity of the reflection mirror is observed at a position twice as large as the position of the SD-OCT signal, that is, in the vicinity of the horizontal axis x=120 in accordance with the theory (refer to Non-patent Document 2) of the intensity-interferometric spectral-domain tomographic imaging apparatus. The height of the signal in this case is proportional to the square of the reflectivity of the measured target (reflection mirror).

In the present invention, an unnecessary signal is observed also at the same position (that is, in the vicinity of horizontal axis x=60) as the SD-OCT signal in part (a) of FIG. 3, but the unnecessary signal becomes imaginary values. Therefore, by using only the real part of the calculation result, it is possible to accurately separate an aimed signal having information about the measured target, and it is possible to obtain a clear tomographic image.

As a means for changing the phase by π, the reference mirror is located on the fine motion stage driven by the piezo element and is moved frontward and rearward; however, instead, the measured target may be located on the fine motion stage.

By using the change of a geometric phase, in place of the fine motion stage, generated by controlling polarization states of the reference light and the measurement light using a polarization plate, a ¼ wavelength plate, a ½ wavelength plate, and the like, a phase difference it may be introduced (refer to Non-patent Document 3).

When performing the above-described calculation, the setting of the spectral interference fringe intensity before and after phase shift may be in a switched manner as represented by Expression (3).

$$C(\omega')=I_1(\omega_0-\omega')\times I_2(\omega_0+\omega') \quad (3)$$

Embodiment 2

Figure 4:
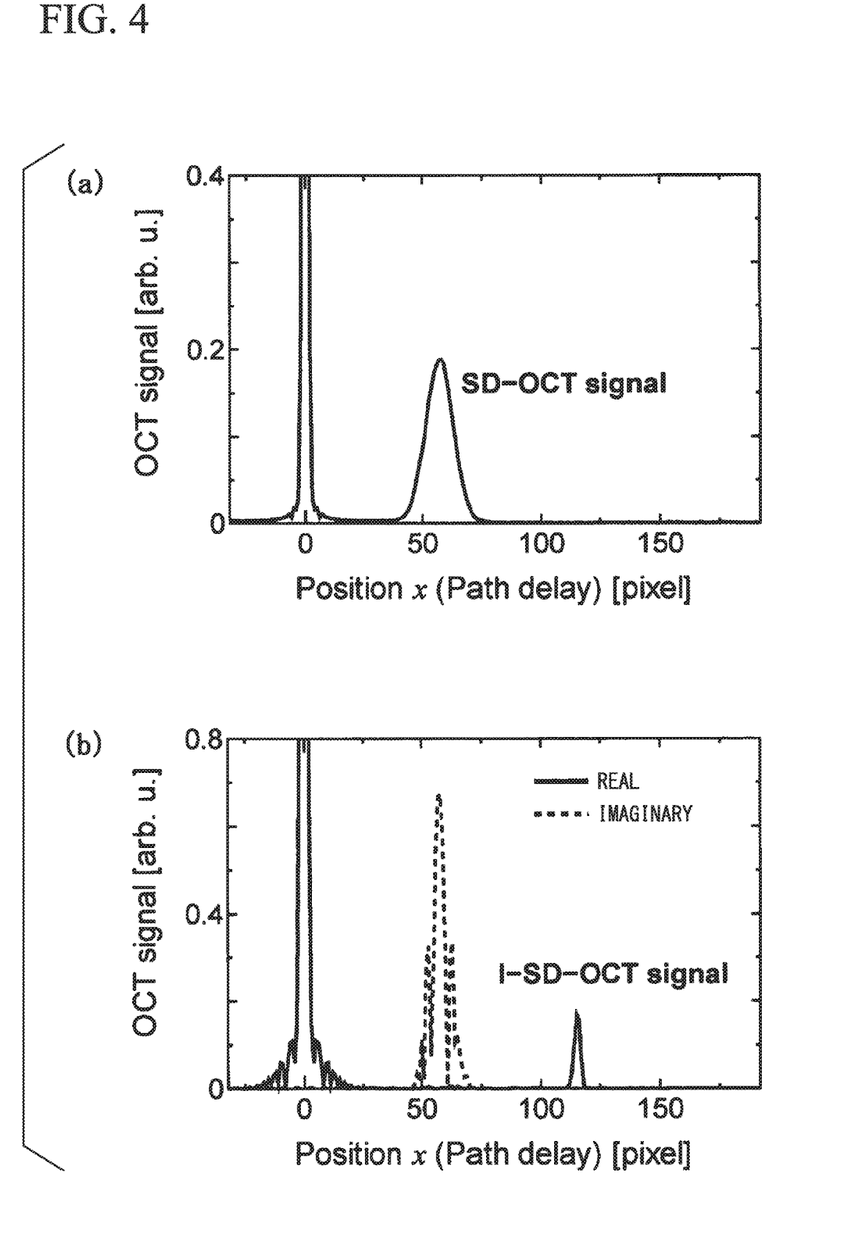
FIG. 4 is a view for comparing similar experimental results when a dispersion medium (dense flint glass) is arranged on a measurement optical path immediately before the measured target. A converted value of a pixel to a length in the present invention (b) is half of that in the SD-OCT apparatus (a).

FIG. 4 shows a similar experimental result when a dense flint glass which is an example of a dispersion medium is arranged on a measurement optical path immediately before the measured target in order to evaluate the effect of dispersion of the proposed apparatus.

Part (a) of FIG. 4 represents a result acquired using a conventional SD-OCT apparatus. Part (b) of FIG. 4 represents a result acquired using the proposed apparatus.

It is found that: in part (a) of FIG. 4, the signal of conventional SD-OCT is broadened due to the effect of dispersion to cause degradation of resolution; but in part (b) of FIG. 4 of the present invention, the width of the aimed signal is not changed from the result shown in part (b) of FIG. 3, and no change subject to the effect of dispersion is seen at all, and therefore, reduction of resolution does not occur.

Embodiment 3

The present invention is described using FIG. 1.

In the optical system of the intensity-interferometric spectral-domain tomographic imaging apparatus shown in FIG. 1 in Embodiment 1, a reference mirror is located on a fine motion stage which is driven by a piezo element, and the fine motion stage is movable frontward and rearward along the propagation direction of light.

However, in Embodiment 3, the fine motion stage is unnecessary, and a general reference mirror distance adjustment mechanism (not shown, for example, a translation stage) included in the prior and existing SD-OCT apparatus may be provided.

In FIG. 1, for convenience, the reference mirror is fixed to the fine motion stage.

Similarly to Embodiment 1, spectral interference fringe intensity, on the basis of a reference mirror and a measured target, detected by a detector which is adjusted such that the center frequency $\omega_0$ of incident light is matched to the center of the detector is stored in a computer (including a display device).

Similarly to Embodiment 1, with respect to the spectral interference fringe intensity $I(\omega)$ converted to be a function of frequency $\omega$ using Expression 1, the spectral interference fringe intensity at a frequency (referred to as positive sideband waves) shifted in a positive direction by $\omega'$ from the center frequency $\omega_0$ is $I(\omega_0+\omega')$, and the spectral interference fringe intensity at a frequency (referred to as negative sideband waves) shifted in a negative direction by $\omega'$ from the center frequency $\omega_0$ is $I(\omega_0-\omega')$.

The product of $I(\omega_0+\omega')$ and $I(\omega_0-\omega')$ is represented by Expression (4).

$$C(\omega')=I(\omega_0+\omega')\times I(\omega_0-\omega') \quad (4)$$

Fourier transform of $C(\omega')$ as a function of $\omega'$ is performed with respect to $\omega'$ in the computer (including a display device).

As a result, the Fourier transform of $C(\omega')$ always gives real values, and an unnecessary signal is also observed adjacently. However, by adjusting the position of the reference mirror using the translation stage similarly to conventional SD-OCT, an aimed signal having information about the position and the reflectivity of the measured target can be separated from the unnecessary signal and can be obtained.

Figure 6:
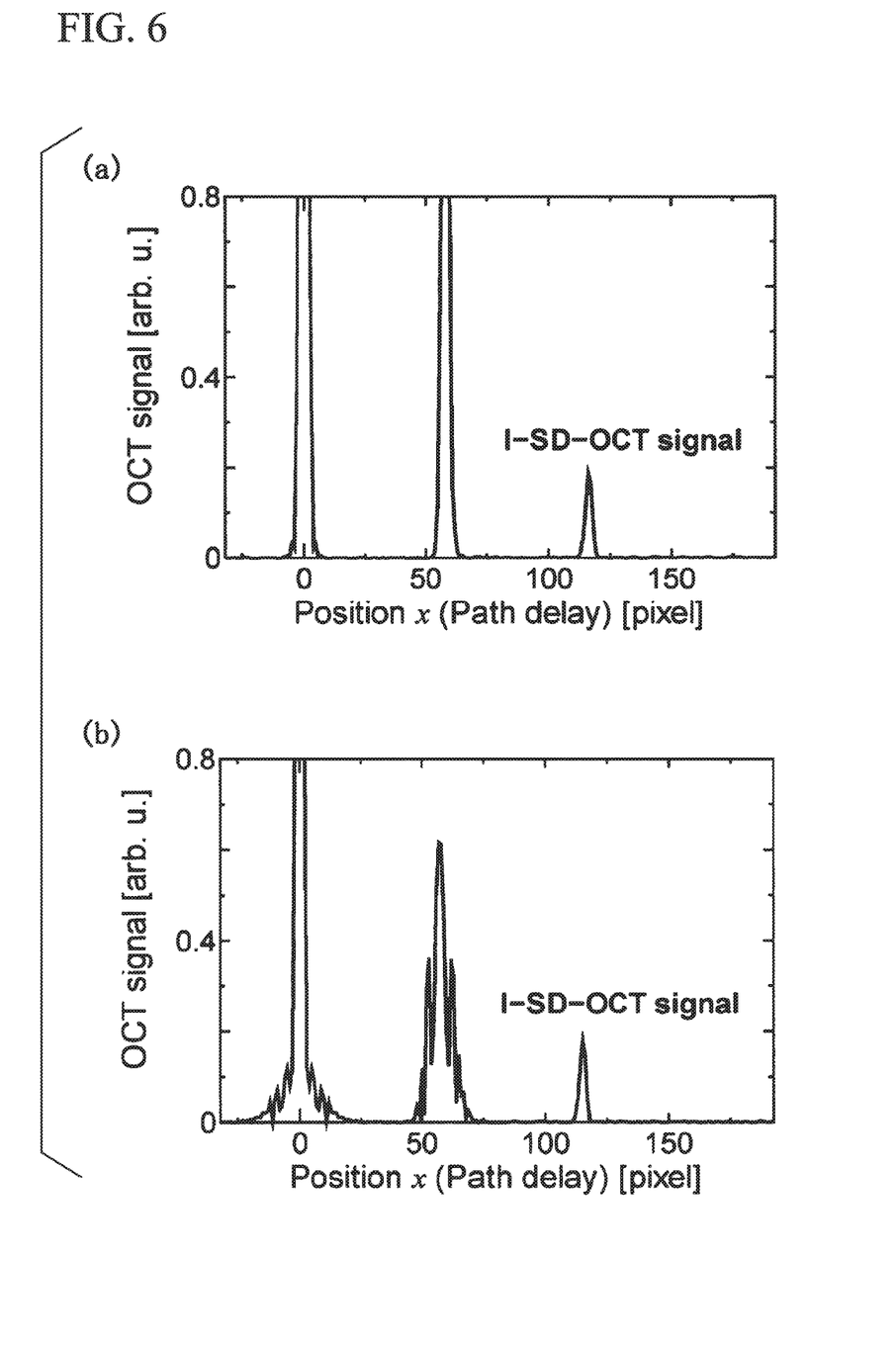

Part (a) of FIG. 6 shows the absolute value of Fourier transform of $C(\omega')$ obtained by the above calculation.

This figure shows an experimental result acquired using the proposed apparatus when a simple reflection mirror is located as the measured target. A corresponding experimental result acquired using a conventional SD-OCT apparatus is shown in part (a) of FIG. 3.

In comparison with the corresponding experimental result acquired using the conventional SD-OCT apparatus shown in part (a) of FIG. 3, in the proposed apparatus, a signal that depends on the reflectivity of the reflection mirror is observed at a position twice as large as the position of the SD-OCT signal, that is, in the vicinity of the horizontal axis x=120.

The height of the signal in this case is proportional to the square of the reflectivity of the measured target (reflection mirror).

In the present invention, an unnecessary signal is observed also at the same position (that is, in the vicinity of horizontal axis x=60) as the SD-OCT signal in part (a) of FIG. 3.

However, by adjusting the position of the reference mirror and increasing the difference between a distance to the measured target (reflection mirror) from the beam splitter and a distance to the reference mirror from the beam splitter, it is possible to separate an aimed signal and an unnecessary signal, and therefore, it is possible to acquire only the aimed signal having information about the measured target.

Part (b) of FIG. 6 shows a similar experimental result when a dense flint glass which is an example of the dispersion medium is arranged on the measurement optical path immediately before the measured target.

A corresponding experimental result acquired using a conventional SD-OCT apparatus is shown in part (a) of FIG. 4.

It is found that, similarly to Embodiment 2, in part (b) of FIG. 6 of the present invention, the width of the aimed signal is not changed from the result shown in part (a) of FIG. 6, and no change subject to the effect of dispersion is seen at all, and therefore, reduction of resolution does not occur.

By adjusting the position of the reference mirror as described above, the aimed signal can be separated from an adjacent unnecessary signal and can be acquired.

Embodiment 4

It is known that, when acquiring a tomographic image of a general measured target based on the principle, even at a position where an object (measured target) is not actually present, an unnecessary image (artifact) occurs inside the image of the object.

Light reflected from each of reflection surfaces present at the measured target interferes to thereby generate the artifact, and therefore, when the reflection surfaces are discrete and the number of the reflection surfaces is N, the number of artifacts is $N\times(N-1)/2$.

It is clear, in the theory (refer to Non-patent Document 2) of the intensity-interferometric spectral-domain tomographic imaging apparatus, that the magnitude of the artifact changes depending on the center frequency $\omega_0$ of incident light.

In order to obtain an effect equivalent to this, in the optical system of the intensity-interferometric spectral-domain tomographic imaging apparatus shown in FIG. 1, the detector included in the spectroscope device is moved in the dispersion direction of the spectrum in a range of about a few percent of the dimension of the detector.

In this way, it is possible to change only the magnitude of the artifact almost without changing the aimed signal having information about the measured target.

When the reflection surfaces of the measured target are discrete, and the number of the reflection surfaces is N=2, the number of artifacts is one according to the above described formula.

Figure 7:
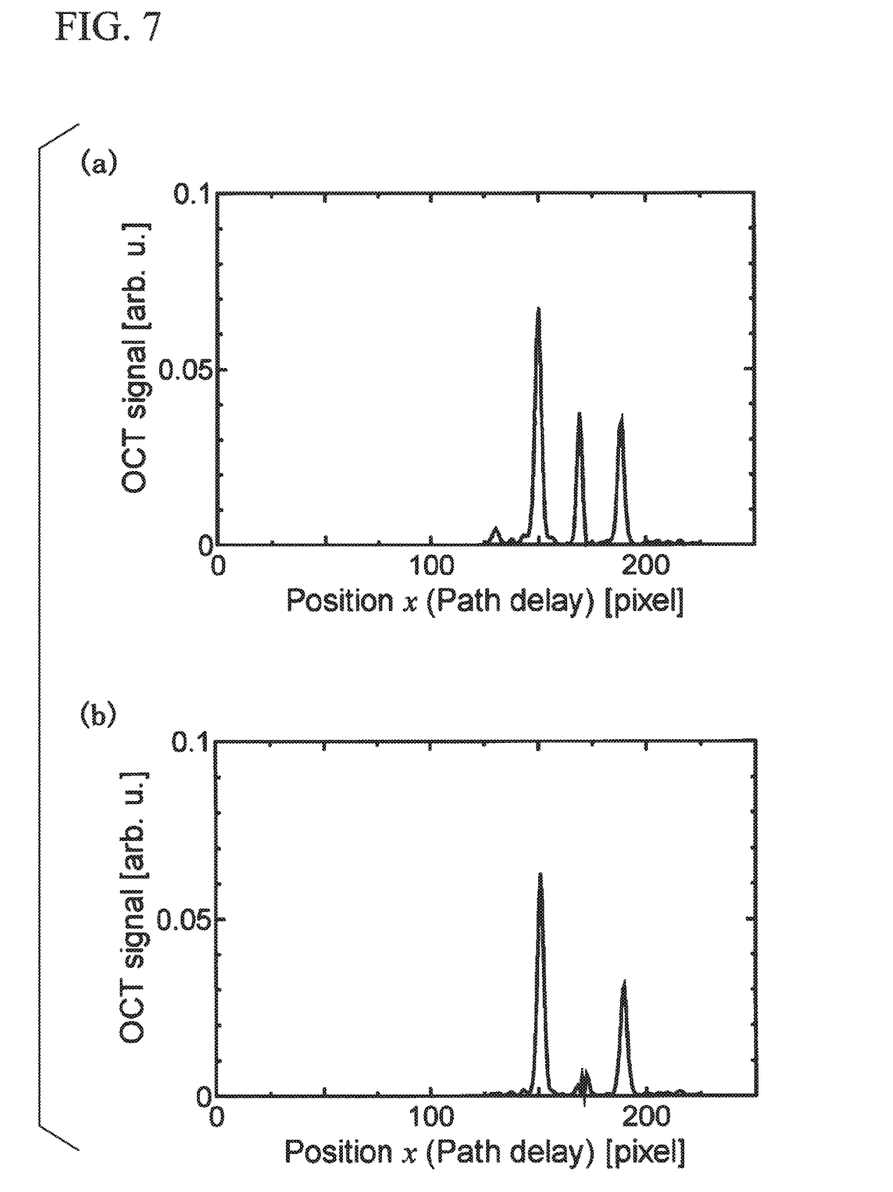

FIG. 7 shows an experimental result acquired using the proposed apparatus when a cover glass for a microscope is used as a measured target in which two discrete reflection surfaces described above are present.

In FIG. 7, only the aimed signal having information about the measured target including the artifact is displayed.

Part (a) of FIG. 7 represents a signal acquired before moving a detector, and part (b) of FIG. 7 represents a signal acquired after moving the detector having 2048-pixel structure in the dispersion direction of the spectrum by a distance of about six pixels along the dispersion direction.

In part (a) of FIG. 7, it is observed that signals corresponding to two reflection surfaces of the measured target and an artifact at a middle position between the signals are present.

However, in part (b) of FIG. 7, it is observed that only the artifact at the middle position is reduced, and the signals corresponding to the two reflection surfaces of the measured target almost do not change.

When the reflection surface continuously changes, or when the number of the reflection surfaces is N=3 or more even when the reflection surfaces of the measured target are discrete, all artifacts cannot be removed only by adjusting the position of the detector.

In this case, it is possible to remove the artifacts by changing the movement distance of the detector to acquire a plurality of data and performing an averaging process of the data.

It is also possible to obtain a similar result by performing simulation of the movement of the detector in a computer and performing signal processing of the simulation result when acquiring the spectral intensity without physically moving the detector.

In the above embodiments, data processing in the computer is performed using a program coded in a Visual C++ (registered trademark) language. However, the type of the information processing apparatus is arbitrary as long as a similar result can be obtained, and the program may be coded and performed using another programming language.

INDUSTRIAL APPLICABILITY

The intensity-interferometric spectral-domain tomographic imaging apparatus that acquires in a time-series manner and uses two spectral interference fringe intensities before and after a phase difference of π is introduced into the reference light or the measurement light in the present invention can be used for existing medical apparatuses for tomographic diagnosis of fundus, tomographic diagnosis of tooth, tomographic diagnosis of skin, and the like.

As a candidate for which the feature of being unaffected by dispersion of a measured target is advantageous, it is expected that the feature is effective especially for diagnosis of the inside of a tooth root buried in gums.

Further, by appropriately selecting the wavelength band of light to be used, the apparatus is applicable also to diagnosis of the inside of an industrial material.

DESCRIPTION OF THE REFERENCE SYMBOLS

1: light source (Source)
2: beam splitter (BS1)
3: measured target (Sample)
4: reference mirror (Reference Mirror)
5: fine motion stage which is driven by a piezo element (PZT)
6: diffraction grating and detector (Grating, Detector)
7: computer (including a display device) (Computer)
8: beam splitter (BS2)
9: diffraction grating and detector (Grating, Detector)
10: diffraction grating and detector (Grating, Detector)

The invention claimed is:

1. An intensity-interferometric spectral-domain tomographic imaging method for generating a tomographic image of a measured target based on information about interference light between measurement light and reference light, comprising:

providing a light source, a reference mirror, a demultiplexer/multiplexer, a spectroscope element, a detector, a computer (including a display device), and a means for generating a phase difference π between the measurement light and the reference light;

forming a spectrometer of the spectroscope element and the detector;

separating light emitted from the light source using the demultiplexer/multiplexer;

acquiring, using the spectrometer, information about spectral interference fringe intensity of interference light obtained by multiplexing measurement light obtained by one separated light being incident on and reflected from the measured target and reference light obtained by the other separated light being reflected by the reference mirror again using the demultiplexer/multiplexer to interfere;

subsequently, acquiring, using the spectrometer, information about spectral interference fringe intensity of light obtained by multiplexing the measurement light and the reference light which is shifted by a phase difference π on the light travel path on the basis of the means again using the demultiplexer/multiplexer to interfere; and performing a Fourier transform calculation based on information about the two spectral interference fringe intensities acquired in a time-series manner and generating the tomographic image of the measured target from a position of a real part of a complex signal obtained as a result of the Fourier transform calculation which appears at a twice distance of a position of an imaginary part of the complex signal.

2. The intensity-interferometric spectral-domain tomographic imaging method according to claim 1, wherein
the demultiplexer/multiplexer is any of a beam splitter and an optical fiber coupler.

3. The intensity-interferometric spectral-domain tomographic imaging method according to claim 1, wherein
the means is formed of a piezo-driven stage that supports the reference mirror, and
a phase difference π to the measurement light is generated in the reference light path by displacing the piezo-driven stage.

4. The intensity-interferometric spectral-domain tomographic imaging method according to claim 1, wherein
the means is formed of a piezo-driven stage that supports the measured target, and
a phase difference π to the reference light is generated in the measurement light path by displacing the piezo-driven stage.

5. The intensity-interferometric spectral-domain tomographic imaging method according to claim 1, wherein
the means generates a phase difference π between the measurement light and the reference light by using a change of a geometric phase generated by controlling polarization states of the reference light and the measurement light.

6. The intensity-interferometric spectral-domain tomographic imaging method according to claim 1, wherein
an artifact that appears in the generated tomographic image of the measured target is removed by acquiring and averaging a plurality of pairs of the two spectral interference fringe intensities acquired in a time-series manner.

7. The intensity-interferometric spectral-domain tomographic imaging method according to claim 1, wherein
an artifact that appears in the tomographic image of the measured target is reduced or removed by slightly moving the detector in a dispersion direction of a spectrum.

8. The intensity-interferometric spectral-domain tomographic imaging method according to claim 7, wherein
an artifact that appears in the tomographic image of the measured target is reduced or removed using information acquired by performing simulation of movement of the detector in the computer without physically moving the detector.

9. The intensity-interferometric spectral-domain tomographic imaging method according to claim 1, wherein
an artifact that appears in the tomographic image of the measured target is reduced or removed by acquiring and applying an averaging process on a plurality of pairs of two spectral interference fringe intensities acquired after slightly moving the detector in a dispersion direction of a spectrum.

10. The intensity-interferometric spectral-domain tomographic imaging method according to claim 9, wherein
an artifact that appears in the tomographic image of the measured target is reduced or removed using information acquired by performing simulation of movement of the detector in the computer without physically moving the detector.

11. An optical tomographic imaging apparatus, comprising:
a light source, a reference mirror, a demultiplexer/multiplexer, a spectroscope element, a detector, and a computer (including a display device), wherein
the apparatus performs an intensity-interferometric spectral-domain tomographic imaging method according to claim 1.

12. An intensity-interferometric spectral-domain tomographic imaging program and a medium storing the program, the program comprising, in the optical tomographic imaging apparatus according to claim 11:
causing the computer to read the information about spectral interference fringe intensity of interference light acquired by the spectrometer;
performing the predetermined Fourier transform calculation;
generating the tomographic image of the measured target from a real part of a complex signal or a real signal obtained as a result of the predetermined Fourier transform calculation; and
displaying the tomographic image on the display device.

13. An intensity-interferometric spectral-domain tomographic imaging method for generating a tomographic image of a measured target based on information about interference light between measurement light and reference light, comprising:
providing a light source, a reference mirror, a demultiplexer/multiplexer, a spectroscope element, a detector, and a computer (including a display device);
forming a spectrometer of the spectroscope element and the detector;
separating light emitted from the light source using the demultiplexer/multiplexer;
acquiring, using the spectrometer, information about spectral interference fringe intensity of interference light obtained by multiplexing measurement light obtained by one separated light being incident on and reflected from the measured target and reference light obtained by the other separated light being reflected by the reference mirror again using the demultiplexer/multiplexer to interfere; and performing a Fourier transform calculation based on a product of two spectral interference fringe intensities of sideband waves which are generated from the acquired spectral interference fringe intensity and are shifted by ω' from a center frequency of light emitted from the light source, extracting a part having information about a reflectivity and a position of the measured target from a real signal obtained as a result of the Fourier transform calculation, and generating the tomographic image of the measured target.

14. The intensity-interferometric spectral-domain tomographic imaging method according to claim 13, wherein
the demultiplexer/multiplexer is any of a beam splitter and an optical fiber coupler.

15. The intensity-interferometric spectral-domain tomographic imaging method according to claim 13, wherein
an artifact that appears in the tomographic image of the measured target is reduced or removed by acquiring and applying an averaging process on a plurality of individual spectral interference fringe intensities acquired after slightly moving the detector in a dispersion direction of a spectrum.

16. The intensity-interferometric spectral-domain tomographic imaging method according to claim 15, wherein
an artifact that appears in the tomographic image of the measured target is reduced or removed using information acquired by performing simulation of movement of the detector in the computer without physically moving the detector.

17. The intensity-interferometric spectral-domain tomographic imaging method according to claim 13, wherein
an artifact that appears in the tomographic image of the measured target is reduced or removed by slightly moving the detector in a dispersion direction of a spectrum.

18. The intensity-interferometric spectral-domain tomographic imaging method according to claim 17, wherein
an artifact that appears in the tomographic image of the measured target is reduced or removed using information acquired by performing simulation of movement of the detector in the computer without physically moving the detector.

19. An optical tomographic imaging apparatus, comprising:
a light source, a reference mirror, a demultiplexer/multiplexer, a spectroscope element, a detector, and a computer (including a display device), wherein
the apparatus performs an intensity-interferometric spectral-domain tomographic imaging method according to claim 13.

20. An intensity-interferometric spectral-domain tomographic imaging program and a medium storing the program, the program comprising, in the optical tomographic imaging apparatus according to claim 19:
causing the computer to read the information about spectral interference fringe intensity of interference light acquired by the spectrometer;
performing the predetermined Fourier transform calculation;
generating the tomographic image of the measured target from a real part of a complex signal or a real signal obtained as a result of the predetermined Fourier transform calculation; and
displaying the tomographic image on the display device.

* * * * *